United States Patent [19]

Wander et al.

[11] 4,030,406

[45] June 21, 1977

[54] APPARATUS FOR STERILIZATION

[76] Inventors: Raoul Wander, 11 bis rue Jean Goujon, 75 Paris 8eme; Robert Angue, 9 La Bastide, Chemin du Puy St., 06600 Antibes, both of France

[22] Filed: Oct. 3, 1972
(Under Rule 47)

[21] Appl. No.: 294,578

Related U.S. Application Data

[63] Continuation-in-part of Ser. No. 93,015, Nov. 27, 1970, abandoned, which is a continuation-in-part of Ser. No. 718,044, April 2, 1968, abandoned.

[30] Foreign Application Priority Data

Apr. 18, 1967  France .......................... 67.103192
Dec. 15, 1967  France .......................... 67.132589

[52] U.S. Cl. .................... 99/461; 21/91;
99/466; 259/10
[51] Int. Cl.² ...................... A23C 3/00; A23L 3/00
[58] Field of Search .................... 99/460, 461, 466;
259/DIG. 30, 9, 10; 21/91

[56] References Cited
UNITED STATES PATENTS 1,624,037  4/1927  Butler ..................... 259/DIG. 30 X
2,148,178  2/1939  Shropshire .............. 259/DIG. 30 X
2,153,537  4/1939  Heath ...................... 259/DIG. 30 X
2,339,735  1/1944  Smith ..................... 21/91
2,339,737  1/1944  Hulse ..................... 21/91
2,570,081  10/1951 Szczenlowski ................. 99/451 X
2,612,354  9/1952  Dron ...................... 259/DIG. 30 X
2,644,740  7/1953  Dodds ..................... 21/91

Primary Examiner—Leonard D. Christian
Assistant Examiner—A. I. Cantor
Attorney, Agent, or Firm—William D. Stokes

[57] ABSTRACT

An apparatus for sterilization of thermolabile materials, particularly lacteal, comprising simultaneously subjecting the material to induced internal heating effects and centrifugal force. The internal heating of the product is accomplished by friction arising between the product and a moving surface. The internal heating and centrifugal apparatus of the invention accomplishes sterilization of the product within a fraction of a tenth of a second. The temperature and the centrifugal force to which the product is subjected cooperate to destory microorganisms that may be present, for example, by coagulating the protoplasm of these microorganisms, and by destroying, or at least degrading, the cell walls of the microorganisms.

10 Claims, 16 Drawing Figures

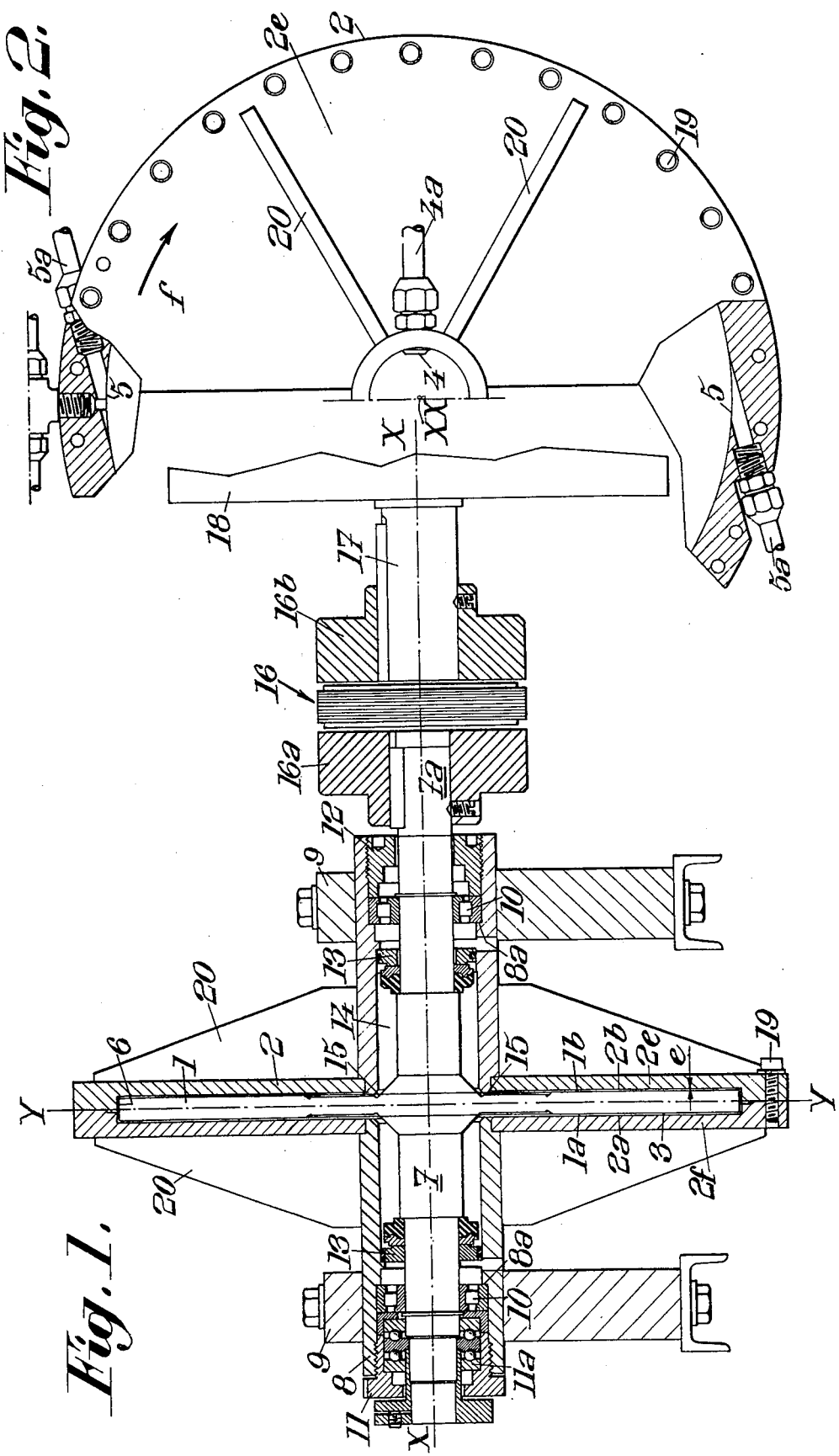

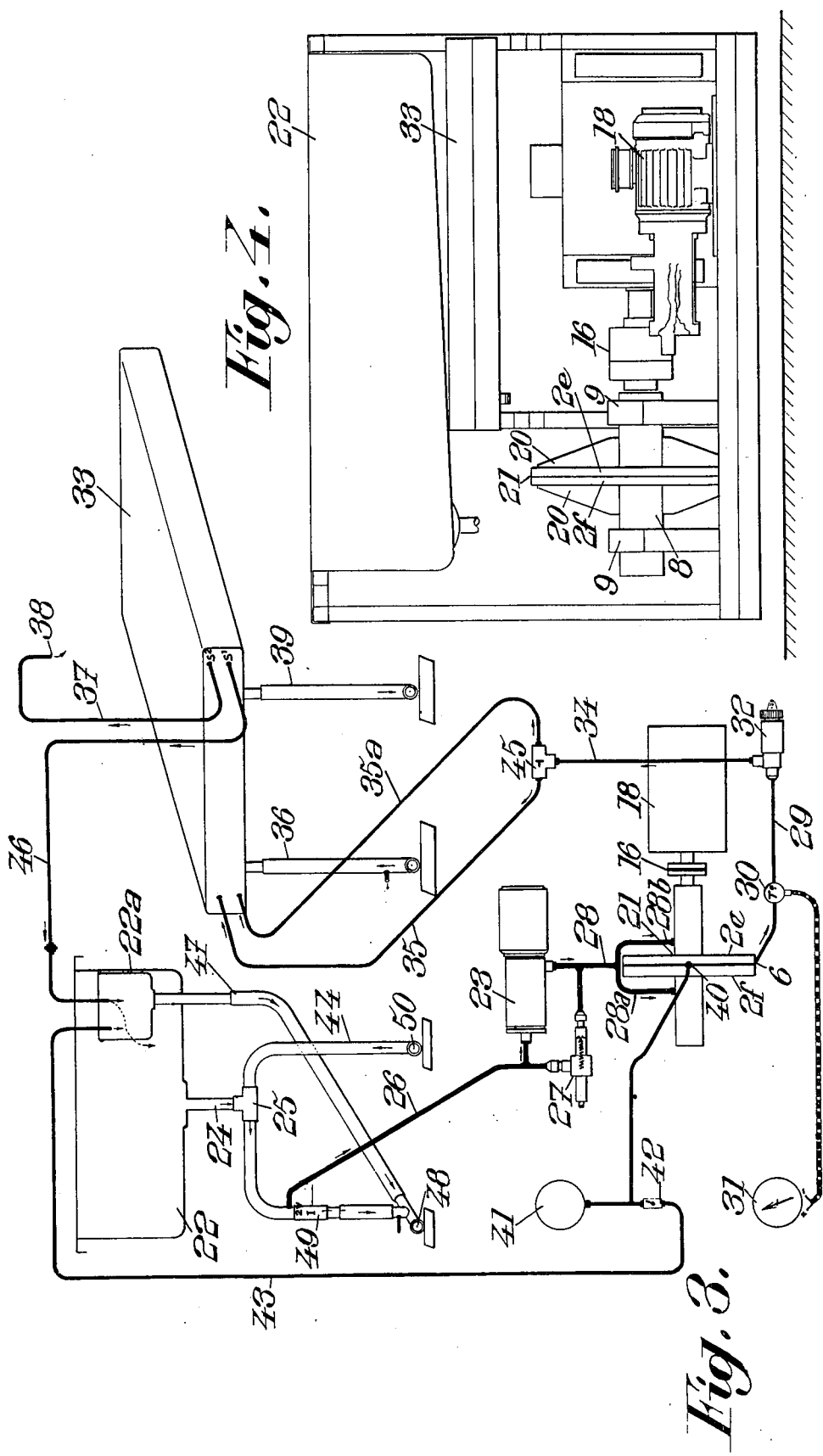

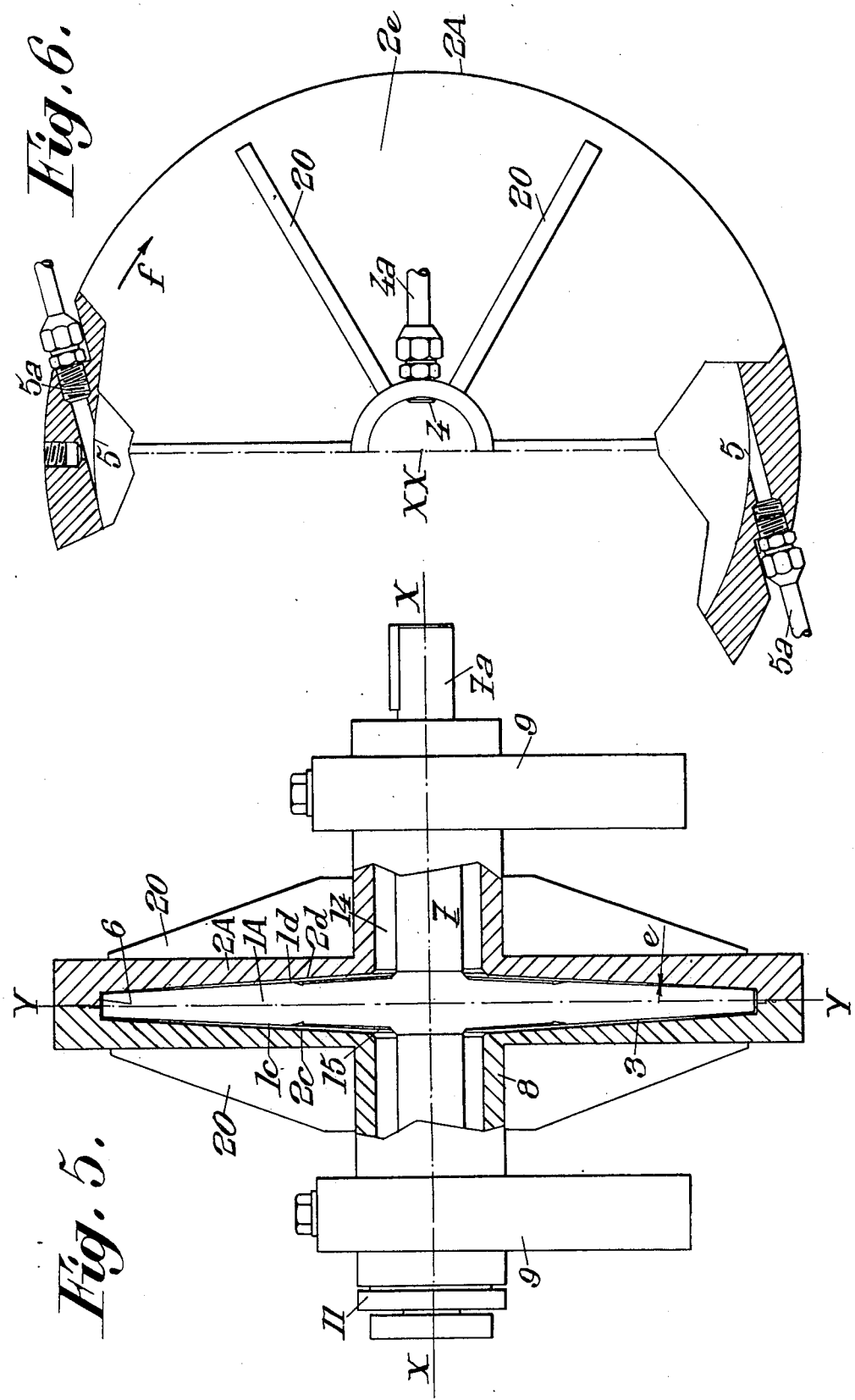

APPARATUS FOR STERILIZATION

This application is a continuation-in-part of copending application Ser. No. 93,015, now abandoned, filed Nov. 27, 1970, which was a Continuation-In-Part of application Ser. No. 718,044, filed Apr. 2, 1968, now abandoned.

The present invention relates to an apparatus for sterilization of liquids, in particular the sterilization of lacteal products, without application of external heat. More specifically, the present invention provides a simple and practical apparatus for sterilizing a liquid, particularly thermolabile substances which cannot be filtered such as lacteal products, plasma and similar biologic materials. The invention provides an apparatus in which the material to be sterilized is simultaneously subjected to internal heating and a centrifugal force. More specifically, the invention is directed to an apparatus for sterilizing a thermolabile product which may contain pathogenic organisms wherein the product is subjected to an internal heating effect by friction against rotating, substantially planar, surfaces in relative movement with respect to the product, to bring and maintain the product in liquid form, for, at most, a few tenths of a second, to a temperature which can assist in destroying any pathogenic organisms which may be present by coagulating the protoplasm of these organisms, and to a centrifugal force adapted to assist in the destruction of the organisms by degrading the cell walls of the organisms. The centrifugal force creates a pressure at the outer periphery of the rotating surfaces which is sufficient to prevent the liquid from boiling, thus making it possible to carry out the treatment in liquid phase.

The apparatus of the invention comprises at least one surface or wall moveable in relative movement to a stationary wall between which the product to be sterilized passes, the speeds of relative displacement of the wall or walls and the product being such that they assure, on the one hand, the bringing of the product to the desired temperature, and on the other hand, the application of a centrifugal force to the particles of the product sufficient to degrade, and even destroy, the cell walls of the microorganisms that may be present in the product to be sterilized.

The apparatus of the invention comprises two members having cooperating opposed substantially planar surfaces spaced apart by less than 0.5 millimeter, inlet means for the charging of the product into the space between the opposed planar surfaced members, an outlet for the discharge of the product between the opposed planar surfaced members, and driving means to produce relative movement of the members at a speed high enough to (1) cause the product to heat to a sterilization temperature in the space and () apply a sufficient centrifugal force to maintain the product in liquid form under pressure in the space sufficient to degrade the cell walls of any organism present, and (3) insufficient to cause thermal shock to the particular product even at sterilization temperatures. Utilizing the inventive apparatus, a sterilized product may be obtained which is substantially identical, with respect to its chemical and physical composition to the initial product, but devoid of organisms.

In the commonly used processes and apparatuses for sterilizing thermolabile materials, the material to be sterilized is subjected to a specified temperature for a pre-determined time period by contacting the material with a heated wall or a hot vapor. By way of example, the sterilization of milk is commonly carried out in bulk at 130° to 150° C. While in the known processes milk is only held at those temperatures for a few tenths of seconds to a few seconds, this seemingly short duration results in deterioration of the organoleptic and nutritive value of the milk. Moreover, the apparatuses commonly used for sterilization have the additional disadvantage of subjecting the milk to a veritable thermal shock, brought about by the subjection of the milk to sudden contact with metal or vapor much hotter than itself resulting in chemical and physical degradation of the material. The chemical degradation more often results in a veritable "cracking" or "crusting" when particles of the product remain stuck to the heated wall of the apparatus while the undesired physical effects are the irreparable segregation or separation of the milk constituents, in particular the cream. In addition, the known methods result in a degree of segregation of the constituents, which often necessitates subsequent homogenization steps to provide a useful product. When vapor methods are used it is necessary to eliminate the water condensed in the product during its sterilization. A major disadvantage of these and other of the known methods, particularly vapor sterilization techniques, is that the laws of numerous countries do not permit their use.

In a practical sense, the only effect on the product brought about by utilizing the novel sterilization apparatus of this invention is the destruction of the microorganisms. The chemical and physical composition of the initial product are unchanged, due, in part to the fact that the thermal treatment of the method is progressive and accomplished in a fraction of a second. In the conventional processes of sterilization by heating, the thermal effect is brutal, brought about, for the most part, by the relatively long duration and suddenness of the intense heating. The known deleterious effects of such methods are chemical degradation and physical segregation and are discussed hereinabove. The apparatus according to the present invention provides all of the useful benefits of sterilization, while overcoming the disadvantages of degradation and segregation brought about in the known processes. The tremendously unexpected improvements in sterilization brought about by the invention have been attributed in part to the fact that the centrifugal force applied have a disruptive effect on the cell walls of the microorganisms while internal heating kills the pathogenic organisms in a very short time. It is, of course, essential to the invention that the walls of the apparatus not be heated to a temperature greater than that of the liquid to be sterilized. This, so to speak, non-heating of the walls, prevents any thermal shock with consequent chemical degradation or physical segregation of the various constituents of the product to be sterilized. Utilizing the present invention, only the microorganisms, that may be present are destroyed, the destruction being total. It was also surprisingly discovered that the process of the invention permits sterilization of thermolabile liquids at lower temperatures and in a shorter time than in the processes heretofore known.

The invention will now be described by the following detailed descriptions in reference to preferred embodiments as illustrated in the accompanying drawings wherein:

FIG. 1 is a cross-sectional view of an embodiment of the invention having a rotatingly driven disc substantially planar with the interior walls of a fixed housing;

FIG. 2 is a fragmentary view, partly in section of FIG. 1 taken on the plane of line Y—Y;

FIG. 3 is a schematic illustration of a sterilizing system embodying the method and apparatus of the invention;

FIG. 4 shows lateral elevation the disposition of a sterilizing apparatus of the type illustrated in FIGS. 1, 5 and 6 in the system of FIG. 3;

FIG. 5 is a longitudinal fragmentary view, partly in section, of another embodiment of the invention wherein the rotating disc member is outwardly tapered from its axis to its periphery;

FIG. 6 is a fragmentary view, partly in section, of FIG. 5 taken along line Y—Y;

Figure 13:
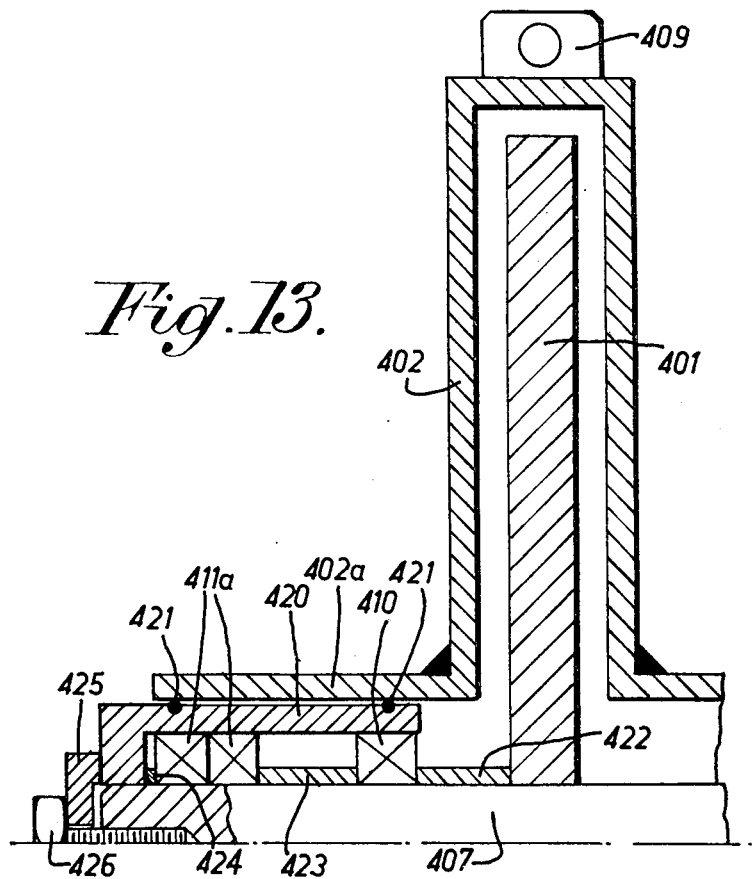
FIG. 13 is a fragmentary view in section of another embodiment of the invention having a rotatingly driven disc substantially planar with the interior walls of a housing.

Referring to FIGS. 1 and 2, there is shown a device of the invention comprising a flat disc 1 mounted on shaft 7. Disc 1 is adapted to be rotatingly driven in the direction of the arrow f, about its axis XX at the interior of a housing or casing 2. The internal walls of casing 2 (2a and 2b) are substantially coplanar with the respectively moveable faces 1a and 1b of disc 1. The distance e between each moveable face 1a and 1b of the disc 1 and the corresponding, opposed fixed face 2a and 2b of the casing is less than 0.5. This space is indicated by numeral 3. The product to be sterilized, for example milk, is flowed into the space 3 at inlet 4 in the region of the axis of rotation XX of disc 1 (see also FIG. 3). The sterilized product passes out of the device at outlets 5 in the region of the periphery 6 of disc 1 (see also FIG. 3). The centrifugal force acts on the product from the center (axis XX) towards the periphery 6 of the disc 1. The internal heating of the product is brought about solely by the friction of the particles of this product on the faces 1a and 1b of the disc 1 and on the fixed faces 2a and 2b of the housing 2 with respect to which the product is displaced at high speed. The centrifugal force creates a pressure at the periphery of the disc sufficient to prevent the liquid from boiling inside the apparatus.

In the embodiment illustrated in FIGS. 1 and 2, the flat disc 1 (having a plane of symmetry YY) is carried by a shaft 7 housed in a sleeve 8 itself carried by blocks 9. Shaft 7 rotates at the interior of the sleeve 8 due to roller bearings 10 which are maintained in position against internal shoulders 8a of the sleeve 8 by means of threaded plugs 11 and 12 fitted into the two ends of the sleeve 8. Shaft 7 passes through these two plugs which plug 11 also supports a bearing 11a. Two packings 13 assure a leak proof connection of the two ends of the chamber 14 located between the central parts of the shaft 7 and of the sleeve 8. Chamber 14 communicates with space 3 through the annular passages 15 and inlet 4. In this manner, the supply of the product prior to sterilization may be utilized in chamber 14 to cool the shaft 7 somewhat while warming the product. On one end 7a of the shaft 7, which passes through the corresponding plug 12, is mounted on one of the halves 16a of a coupling 16 whose other half 16b is fixed to the shaft 17 of an electric motor 18.

In FIG. 2, one of the walls 2e forming casing 2 can be seen in a more precise manner. The wall 2e is fixed to the other wall 2f (FIG. 1) by means of pins 19, and both the walls 2e and f have reinforcing ribs 20. Still referring to FIG. 2, there can be seen the inlet 4a for the product to be sterilized opening out at the point 4, and the outlet tubes 5a opening out at the points 5 for the discharge of the sterilized product. FIGS. 5 and 6 illustrate an embodiment of the invention where the rotatable disc 1A is tapered from its axis to its peripheral edge. Thus the faces 1c and 1d of the disc 1A are slightly inclined to the plane of symmetry YY of the disc instead of being parallel to this plane, as in the embodiment of FIG. 1. It is the same for the faces 2c and 2d of the casing 2A which are opposed to the faces 1c and 1d. In the embodiment of FIGS. 5 and 6, as in other embodiments of this invention, the spacing e between the opposed walls 1c–2c on the one hand, and 1d–2d on the other hand, which delimit the space 3, is 0.5 mm or less. Excellent results have been achieved where the distance e between the faces of the rotating disc and the opposed fixed interior wall is of the order of about 0.2 to 0.3 millimeter.

When the product to be sterilized is milk, the temperature is raised to about 135° to 145° C. within a fraction of a tenth of a second and is held at the maximum temperature for only a few tenths of a second. The maximum speed of relative displacement when sterilizing milk (in the neighborhood of the periphery of the disc) is greater than 50 meters per second and preferably of the order of 60 to 80 meters per second.

It was discovered that utilizing the apparatus of the invention, milk remains absolutely stable in the course of the sterilization treatment, even where the milk has an excess of albumen, calcium and/or acidity. Of particular importance is the fact that no coagulation manifests itself in the course of the treatment to the end that the sterilized product remains a complete food with all the nutritive value of the original milk, that is, without loss of vitamins, thiamine, lysine and other amino-acids. Moreover, the digestability of the protein of the milk is not altered by the sterilization treatment.

In FIG. 3, a sterilization system in accordance with the invention is illustrated. The illustrated system incorporates a device, indicated by numeral 21, such as shown in FIGS. 1, 2, 5, 6, and 12, driven by the motor 18 through the coupling 16. In the system, a vat 22 is provided for receiving the product to be sterilized. A drain chamber 22a is provided in vat 22. A pump 23 is provided which is adapted to pump the product to be sterilized from the vat 22 through pipe 24, three-way valve 25 and into conduit 26. By-pass valve 27 is disposed in parallel with the pump 23. The parallel unit 23–27 supplied by conduit 26 discharges into conduit 28 which supplies, by its branches 28a and 28b in parallel, the sterilizing apparatus 21.

An outlet conduit 29 is provided for the sterilized product which exits at periphery 6 of the rotating disc (through the tubes 5a shown in FIG. 2 and FIG. 6). Conduit 29 is provided with a temperature sensor means 30 that is cooperatively connected with a thermometer means for indicating the temperature. A regulator valve means 32, which can be controlled by, for example, a pneumatic means (not shown) is provided to insure a weight of flow such that the sterilized liquid reaches the desired temperature. In the illustrated embodiment, this is achieved by sensor means 30.

A two-zone heat exchanger 33 is connected to receive the sterilized product through the conduits 34 and 35 and cooling water through conduit 36. The sterilized product, which exits through the conduit 37 and is taken off at discharge outlet 38. The water, which is heated by the exhanged of heat with the sterilized product, is discharged through pipe 39. A pressure sensor means 40 is provided and operatively connected with means 41 for indicating the pressure at the interior of the unit 21. Valve means 42 is provided for initially purging the air at the interior of the unit 21. The purged products are returned through the conduit 43 into section 22a of the vat 22. In the illustrated system a water circulation system is provided for testing the sterilization apparatus or for putting this apparatus under load. This water circulation system comprises an inlet 50 and conduit 44. The water flows through valve 25 into conduit 26. A conduit 35a is also provided that can be alternated with conduit 35 by three-way valve 45. Where the alternate conduit 35a is used, the discharge from the exchanger 33 is made through the conduit 46 towards emptying section 22a, emptying pipe 47, thence to discharge outlet 48. Outlet 48 may also be supplied through the valve 25 from conduit pipe 49.

In operation, water is pumped into the system at the inlet 20. The water flows through valve 25 towards conduit 26. Pump 23 pumps the water into conduits 28, 28a and 28b and, from there, into chamber 14 of the unit 21. The friction created by the product movement with respect to planar surfaces in unit 21 heats the water which is then evacuated through the conduits 29, 34 and 25a. The water may be in the liquid or vapor state according to the adjustment temperature. In the exchanger 33 the heated water is cooled by contact with cold water arriving through the pipe 36. The water, thus cooled, exits through conduit 46, and from there, it flows through pipe 47 to discharge outlet 48.

When the apparatus has been thusly started and adjusted, the position of valves 25 and 45 is modified (after the flow of water to inlet 50 has been cut off) to effect flow of the product in vat 22 through the conduits 24 and 26, pump 23 and conduits 28, 28a and 28b into sterilizing unit 21. The sterilized product is discharged at the periphery 6 of unit 21. The sterilized product flows through conduits 29, 34 and 25 to exchanger 33, where it is cooled before being discharged through the conduit 37 and outlet 38.

In FIG. 4, there is shown an enlarged schematic illustration showing vat 22, two-zone exchanger 33 (one zone being for the treated product and the other zone for the test water), sterilizing unit 21, coupling 16 and motor 18 of FIG. 3.

Figure 12:
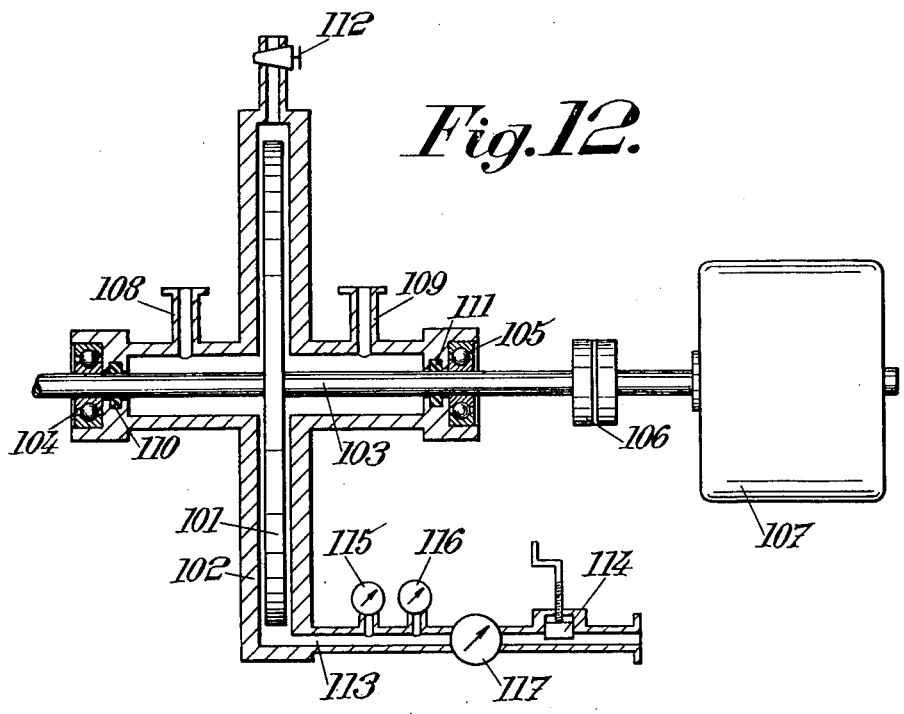
FIG. 12 is a view partly in section, of another embodiment of the invention utilizing a flat rotating disc.

FIG. 12 is a sectional view of another embodiment of a flat disc sterilizer device of this invention. In this embodiment the liquid to be sterilized flows into the sterilizer through conduits 108 and 109. The sterilizer unit comprises a disc 101 mounted rotatably in housing 102. Disc 101 is rigidly mounted on shaft 103. The ends of shaft 103 are journaled through housing 102 by means of, respectively, bearings 104 and 105 and packings 110 and 111. Shaft 103 is driven, through the intermediary of a coupling 106, by means of motor 107. The liquid introduced, either by gravity or by means of a pump, through conduits 108 and 109 flows into the housing adjacent to the shaft 103 on either side of disc 101.

Any air in the installation at commencement of operation is removed by means of a purging valve 112. When the device is in operation the liquid passes between the planar surfaces formed by rotary disc 101 and the inner surfaces of housing 102 adjacent to the disc member and brought to the sterilizing temperature by friction. The effects of centrifugal force degrades the cellular walls of any microorganisms present and causes the liquid to be driven towards the periphery of the disc and thence through outlet conduit 113 provided with a flow regulator device 114. Instruments for measuring the temperature pressure 116 and its rate of flow may be provided as illustrated by means 115, 116 and 117 respectively.

It may be appreciated that the sterilizing temperature may be readily controlled either by varying the speed of rotation of the disc or by varying the rate of flow of the liquid. Utilizing the apparatus just described in which the disc had a diameter of 400 millimeters and a thickness of 15 millimeters, positioned at 0.3 millimeters from the walls and driven at 3,000 revolutions per minute, the temperature reached a maximum of 145° C. for a flow rate of 120 liters/hour.

Summarized in Table I are comparative analyses of some bacteriological counts in cream before and after sterilization utilizing the method and apparatus comprising the rotating disc unit of this invention heretofore described.

TABLE I

BEFORE STERILIZATION

CREAM A

1. Count of thermoresistant anaerobic bacteria (sporulated) after 30 minutes of heating at 80° C. in a medium of deep gelose VF in tubes:
   After 7 days at 37° C. more than 10,000 organisms/1 $cm^3$.

2. Count of thermoresistant aerobic bacteria (sporulated) after 30 minutes of heating at 80° C. in a medium of nutritious gelose in Petri boxes:
   After 3 days at 37° C.:75,000 organisms/ 1 $cm^3$.

3. All germs using the two layer method in a medium of tryptone Agar medium in Petri boxes (Buttiaux):
   After 3 days at 30° C.:more than 10,000,000 organisms/ 1 $cm^3$.
   After 3 days at 6° C.:1,800,000 organisms/1 $cm^3$.

4. Coliform germs on green brilliant broth counted after incubating 48 hours at 30° C.:more than 1,000 organisms/ 1 cm$^3$.

5. Escherichia coli (Mackenzie test) counted after 48 hours at 44° C., on green brilliant broth and peptoned water:more than 1,000 organisms/1 cm$^3$.

6. Pathogenic staphylococcus on Chapman medium:no organisms.

7. Salmonella and Shigella research:no organisms.

AFTER STERILIZATION

Cream B

1. Count of thermoresistant anaerobic bacteria (sporulated) after 30 minutes of heating at 80° C. deep in a medium of gelose VF in tubes:

After 7 days at 37° C.:No organisms.

2. Count of thermoresistant aerobic bacteria (sporulated) after 30 minutes of heating at 80° C. in a medium of nutritious gelose in Petri boxes:

After 7 days at 37° C.:no organisms.

3. Count of all germs using the two layer method in a medium of tryptone Agar in Petri boxes (Buttiaux):

After 3 days at 30° C.:No organisms.

After 3 days at 6° C.:No organisms.

4. Coliform germs on green brilliant broth counted after incubating 48 hours at 30° C.:No organisms.

5. Escherichia coli (Mackenzie test) counted after incubating 48 hours at 44° on green brilliant broth and peptoned water: No organisms.

6. Pathogenic staphylococcus on Chapman medium:no organisms.

7. Salmonella and Shigella research:no organisms.

Figure 7:
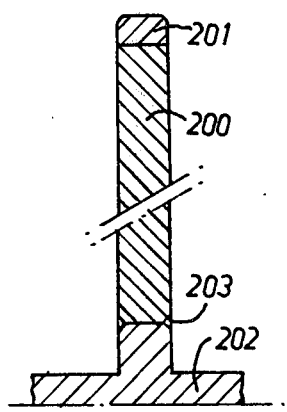
FIG. 7 illustrates the construction of a preferred rotating disc embodiment of the invention.
Figure 8:
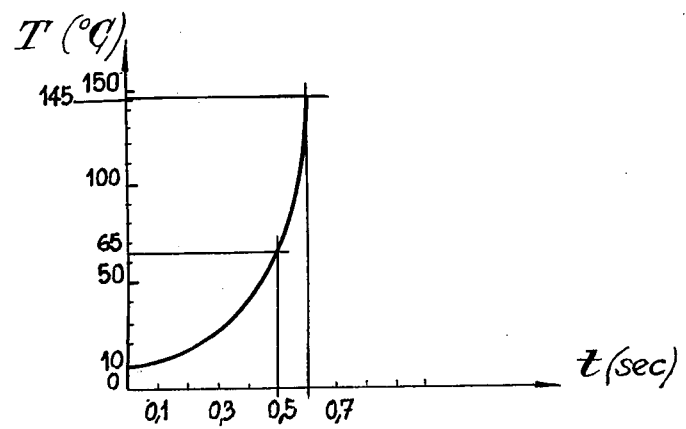
FIG. 8 shows a curve illustrating the rise of temperature (given on the ordinate in degrees C) as a function of the time (given on the abscissa in tenths of a second) in a sterilization apparatus, of the disc type of the invention.

FIG. 8 illustrates the evolution of the temperature as a function of the time in a product sterilized in a device of the type illustrated in FIGS. 1-2, 5-6 or 7. Assuming that the product arrives cold at a temperature of 10° C., it is seen that at the outlet, at the end of 0.6 second, the temperature reaches 145° C., the product being heated progressively without ever being in contact with a wall hotter than itself. This lack of contact with bodies hotter than itself avoids any thermal shock. It will also be noted that the temperature of the product is raised from about 65° to about 145° C. in less than a tenth of a second. Consequently the product remains only a fraction of a second at temperatures which could, if held at such temperature for any greater time period, bring about the degradation in the chemical and physical structure of its components. Utilizing the inventive apparatus, cooling of the product commences immediately after the very transient temperature maximum is reached. It is to be understood, in the case of lacteal products, that it is important to cool the sterilized product rapidly as it exits from the inventive device in order to avoid holding the product at 145° C. after its outlet from the device.

Figure 9:
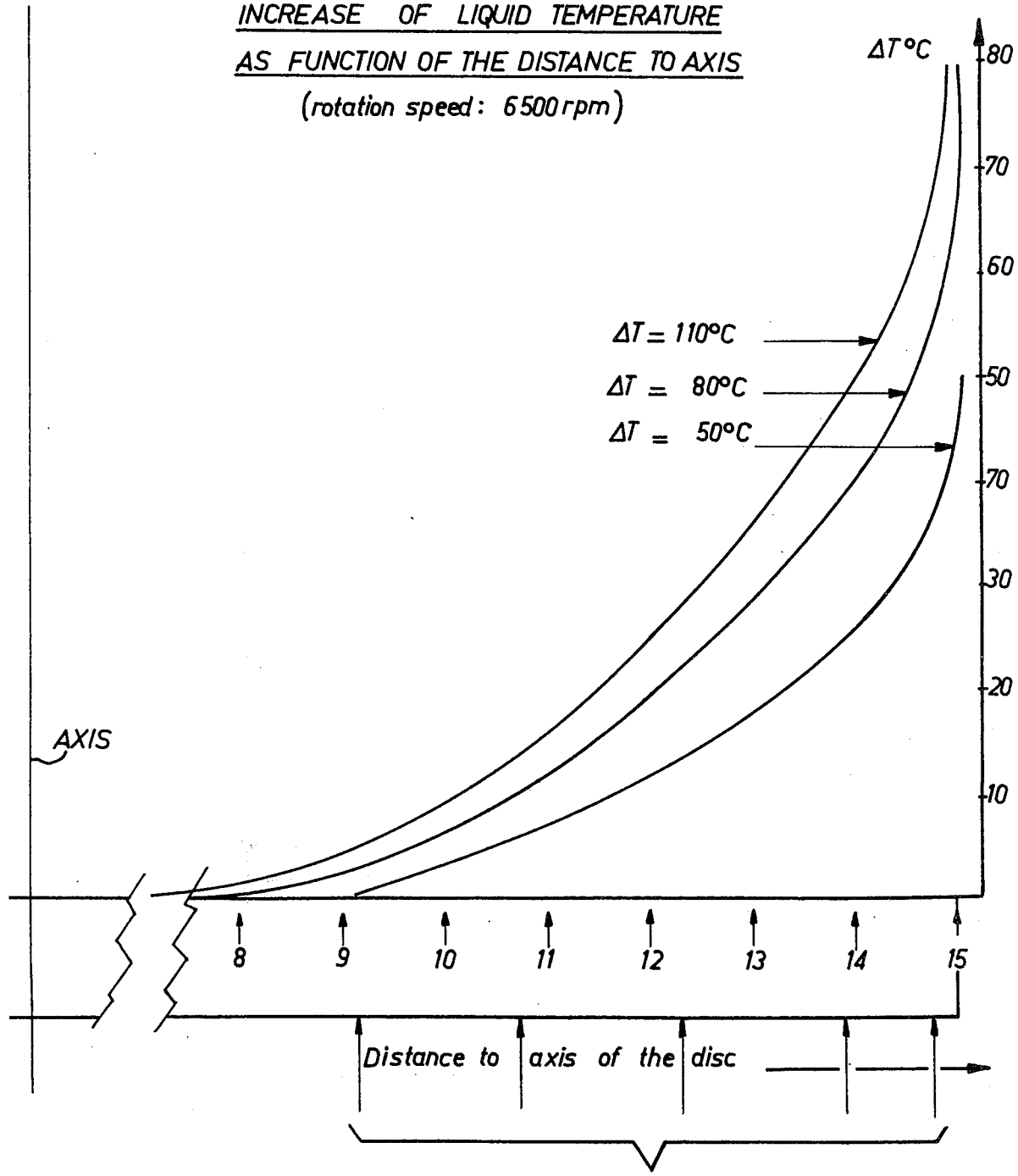
FIG. 9 is a graph illustrating the increase of liquid temperature as a function of the distance to the axis of the disc type embodiment of the invention.
Figure 10:
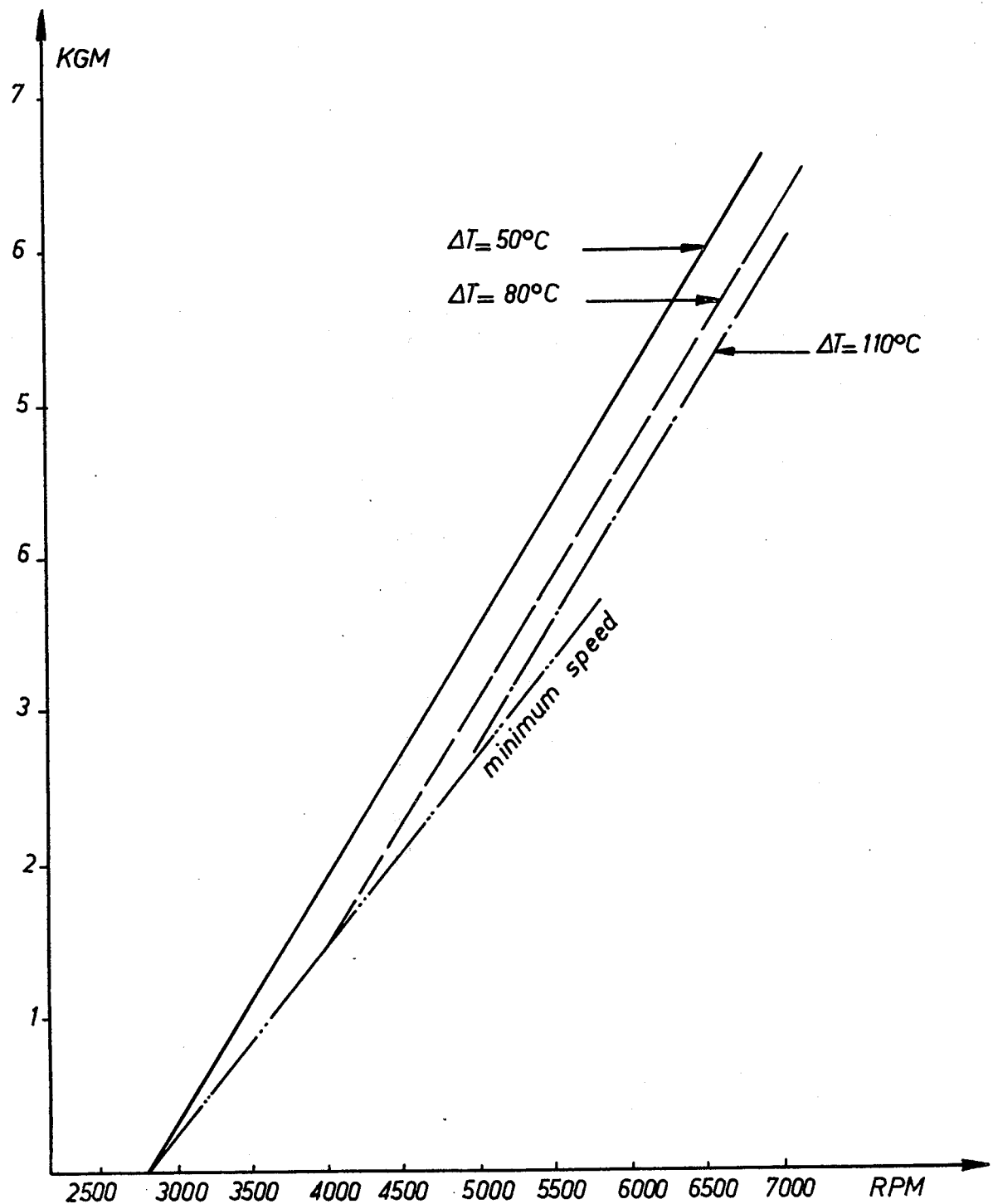
FIG. 10 is a graph illustrating the driving couple absorbed by a rotating disc of the invention.
Figure 11:
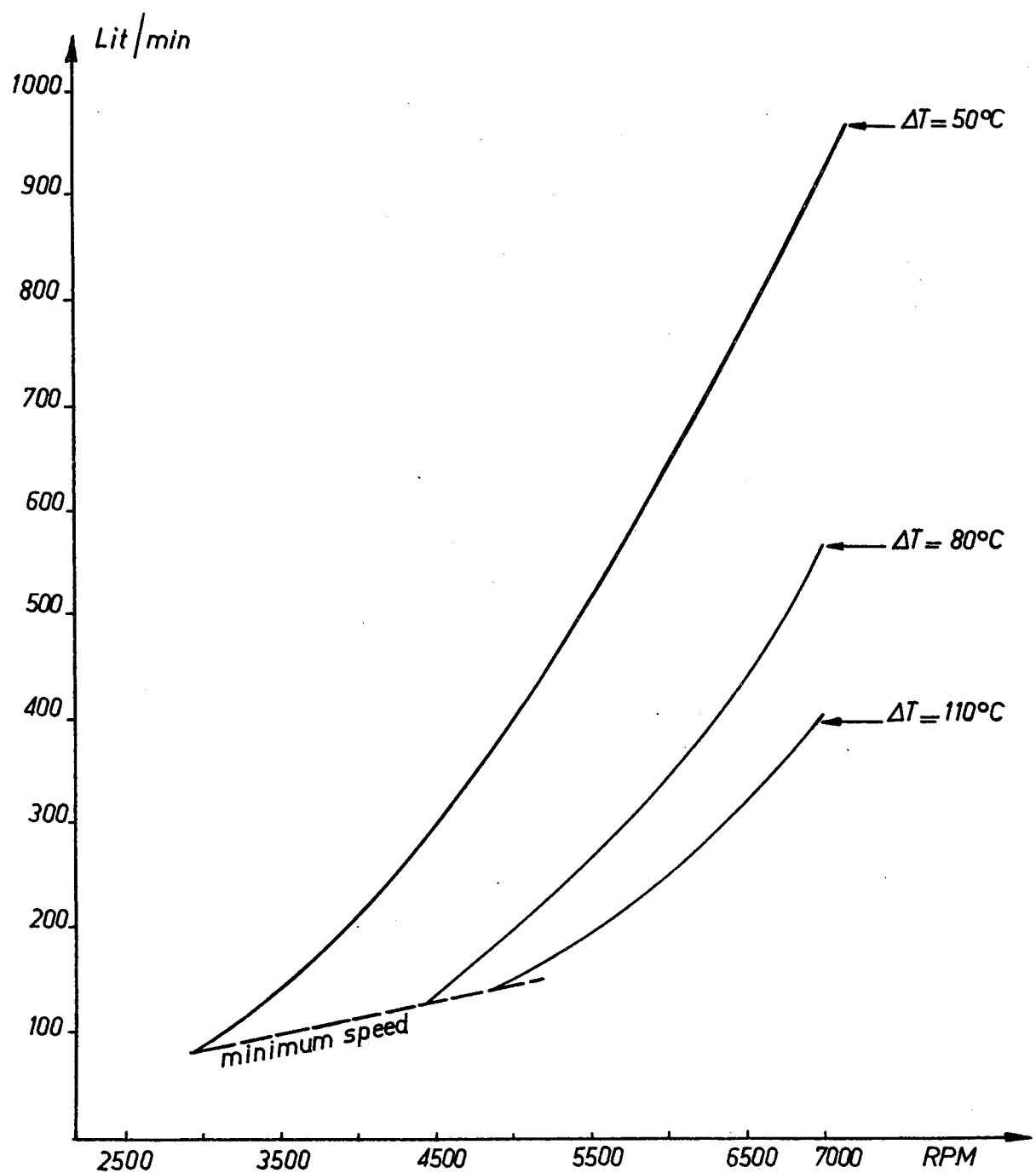
FIG. 11 is a graph illustrating flow as a function of the rotation speed in a sterilizing apparatus of the invention.

An apparatus was constructed incorporating the rotating disc embodiment of FIGS. 1 and 2 and tested in the sterilization of milk. Thermocouples were placed on the walls of the disc along its radius. In operation, the temperature at the point of each thermocouple was noted in accordance with its position on the disc for a given speed of rotation. The speed of rotation was varied during the tests. FIGS. 9, 10 and 11 illustrate the summary of the results of the runs. The three $\Delta$ T curves correspond respectively to temperature differences between the product introduced and the product discharged at 110°, 80°, and 50° C. Referring to FIG. 9 it will be observed that the temperature increase of the milk treated was only noticeable after a certain distance from the axis and that a minimum peripheric speed exists in order to obtain a given temperature increase between the entrance and the exit. It will also be noted that the temperature increase, $\Delta$ T, is perceptibly proportional to $(x-x_o)^4$, in which $x$ represents the abscissa on a radius of the disc and $x_o$ the abscissa, on a radius of the disc, of the disc point where the minimum peripheric speed, as mentioned above, is obtained. The result is that the central part of the disc remains at a low temperature and only the peripheral zone is raised to high temperature. This phenomenon is more noticeable the greater the temperature differential desired between the input to and the discharge from the machine with resulting greater differentials in expansion of the disc. Thus, if a large difference between input and output temperatures, as, for example, where output temperature as high as 160° C., is desired, it is necessary to prevent the expansions developed in the peripheral parts of the disc from causing buckling and jamming because of reduction of the small gap which exists between the housing and the disc.

FIGS. 10 and 11 illustrate respectively, the driving couple absorbed by the disc and flow as a function of the rotation speed. Utilizing speeds varying from 2500 rpm to 7000 rpm, the driving couple absorbed by the disc was measured. The differences in temperature, $\Delta$ T, between the inlet and outlet of the disc were 50°, 80°, and 110° C. It will be observed from the graphs that the variation of the couple is a linear function of the driving speed of the disc. It may also be observed that the driving couple is measurably independent of the differences of temperature between the entrance and the exit of the milk since the graphs corresponding to a $\Delta$ T of respectively 50°, 80° and 110° C. are very close, accordingly, the couple is measurably independent of the flow of fluid through the device. This is so since, when the speed of rotation is varied, the maintenance of constant differences in temperature is obtained by a correlative variation of the flow treated in the device.

It will also be observed from the graphs of FIGS. 9, 10 and 11 that there is a minimum speed of rotation below which it is impossible to obtain a given temperature increase.

In the preferred embodiment, disc 1, shown in FIGS. 1 and 2, disc 1A in FIGS. 5 and 6, disc 101 in FIG. 12, and disc 401 in FIG. 13, are constructed in such manner that the opposed planar surfaces of the apparatus will not seize during operation, no matter what product is being sterilized in the unit. Seizing between the planar surfaces may be avoided in numerous ways, e.g., careful selection of the construction material in accordance with the temperature needed to sterilize the material being handled, and/or careful control of the dimensions of the disc. This latter control will eliminate any possibility of undulations during the high speed rotations. In the preferred embodiment of the invention, the discs are constructed as shown in FIG. 7. It was discovered that such construction completely eliminated seizing brought about by high peripheral sterilizing temperatures, and undulations particularly where large diameter discs are required in high capacity plants. It was discovered that seizing may be simply overcome by employing a disc of a metal, preferably steel, characterized by a high elastic limit and providing an annular collar or ferrule in gripping engagement with the disc around its periphery.

By way of example of such construction, a disc 200 was manufactured 15mm thick having external radius of 130mm. The disc was mounted on and driven by a shaft 202, 40mm in diameter. The disc was welded to the shaft at weldpoint 203. The disc and shaft were of nickel-chromium-molybdenum steel having a 3% copper content, which construction provided, upon heating, a yield strength of at least about 150 kg/mm². A ferrule or collar 201 of the same metal 15mm thick (same thickness as the disc), with a radial diameter of 20mm was heat shrunk on disc 200. The free edges 204 of ferrule 201 were rounded. The dimensions of the ferrule when cold are such that: the diameter of the inner cylindrical surface = diameter of disc $d - (E_1 + E_2)$, where $E_1$ corresponds to the thickness of the disc at the temperature of greatest expansion of the metal during any sterilization operation and $E_2$ corresponds to the adequate metal thickness for developing, at sterilization temperature, a slight flexible compression stress maintaining the ferrule in place.

Figures 14, 15:
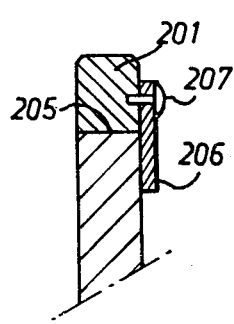
FIG. 14 is a fragmentary view in longitudinal section showing a preferred mode for making a rotating disc of the type shown in FIG. 7.
FIG. 15 is a longitudinal, fragmentary, sectional view showing a modification of the rotating disc of FIG. 7.

Fitting of collar or ring 201 over the disc may be accomplished in any desired manner. FIG. 14 shows a mode for positioning ring 201 on disc 200 wherein the ring is fitted with three brackets 206 fixed by screws 207 and arranged at 120° from each other. In an exemplary case for treating milk at a desired sterilization temperature of 160° C., d equaled 360mm and the internal diameter of the ring cold was 259.4mm, the ring was heated to about 300° C. At this temperature the internal diameter was 260.05mm. The ring was then arranged around disc 200 until the brackets 206 abutted one face of the disc. Collar 201 may be fixed in place by numerous methods, for example, force fitting, and shrink fitting. In the preferred embodiment, the ferrule is mechanically joined to the disc by force fitting and welded together by electron bombardment.

An alternative mode of attaching ring 201 to disc 200 is illustrated in FIG. 15. The ring is pierced by spike 208 driven through it and into disc 200 by a radial force. Four or more such spikes are arranged at regular intervals around the periphery.

It has been established that whatever the kind of operation to which the machine is subjected, no jamming occurs inside the housing within the range provided for the use of the machine despite the small degree of play which exists between the rotating disc and the housing when the disc is provided with the annular ring as described.

It has also been observed that, in the case of apparatus where the housing is fixed axially and especially in the case of a design where the housing is fixed axially only on one side of the housing, disturbances occur in the course of operation if it is desired to achieve high sterilization temperatures, e.g. above 140° C with concomitant high pressures inside the housing to prevent boiling. This is particularly evident when a high sterilization temperature is sought for a relatively low rate of supply. Under the action of high internal pressure, the housing tends to become distorted in an asymmetrical way in relation to the disc so that the disc rubs against the housing.

It has been found that this difficulty can be obviated by fixing the housing in its symmetrical plane, namely at its outer periphery and providing means to permit the housing to slide freely in the axial direction in relation to the axis of the disc.

In a preferred embodiment, the housing is fixed to a base at its outer periphery and the axial zone of the housing includes a laterally-extending, cylindrical member on each side of the housing, which encloses, on both sides of the disc, a sliding sleeve containing the necessary bearings and seals arranged around the shaft of the disc, the sleeves being able to slide freely in relation to the housing. Such an arrangement makes it possible to obtain symmetrical distension of the housing under the action of internal pressures created by the fluid to be sterilized with the result that proper functioning is ensured even in the case of high sterilization temperatures.

In a preferred embodiment of the invention, particularly where the product to be sterilized requires higher temperatures, e.g. 140° C. and above, the sterilization apparatus of the invention is constructed as shown in FIG. 13. In FIG. 13, disc member 401 is shown contained in housing member 402 and rotatably mounted on shaft 407. The housing 402 is attached to a pedestal by means of fixing brackets 409 fitted to the periphery of the housing in its median plane. A seal 410 and ball-bearings 411a are arranged between the shaft 407 and a sleeve 420, which sleeve is free to slide inside the cylindrical axial extension 402a of the housing 402. Two seals 421 are arranged between the sleeve 420 and the cylindrical part 402a. The position of the seal 410 is fixed in relation to the disc 401 by means of a spacer 422 and in relation to the ball-bearings 411a by means of a spacer 423. The unit formed by the seal 410, the ball-bearings 411a and the spacers 422 and 423 is clamped together by means of an element 424. A cap 425, rigidly mounted on the shaft 407 by means of a screw 426 bears against the external surface of the element 424.

In this embodiment the shaft 407, the seal 410, the bearings 411a and the sleeve 420 can slide freely inside the cylindrical part 402a of the housing 402. It is possible to locate the housing centrally in order that, under the influence of an internal pressure the housing may become deformed symmetrically in relation to the disc. During that deformation the play between the housing 402 and the disc 401 consequently always remains the same on the right and the left of the disc, and any rubbing of the disc inside the housing is thus avoided.

Equally, when the throughput being treated is relatively low, an automatic centering of the disc in relation to the housing takes place with the result that the sterilizing temperatures reached on each side of the disc remain constantly the same. An embodiment of that kind is to be recommended whenever the sterilizing temperature desired exceeds about 130° C.

For a given apparatus there is in general a good temperature balance between the two faces of the disc when the torques transmitted to the disc and consequently the rates of supply treated by the apparatus are relatively low. On the other hand, if the rate of supply treated by the machine is increased while the same temperature differential between output and discharge is maintained, there is produced, for high rates of supply, even with a floating housing as described above, a disequilibrium between the maximum temperatures reached on one side and the other of the disc. Seeing that this example of operation corresponds, as can be seen from FIG. 11, to high rates of rotation of the disc, it is clear, according to the curves of FIG. 10, that the torque absorbed by the disc is then very great, and, as can be seen, the forces which tend to automatically center the disc in the housing are insufficient to ensure movement of the disc in relation to the transmission, regard being had to the strong reactions of the elements which drive it.

It has been found that this difficulty can be obviated by placing a temperature-registering element on each side of the disc, in the gaps through which the product being treated passes, the registering elements sending their signals to a relay which controls the rotation of a motor, which allows during the course of operations, relative axial movement of the disc in relation to the housing.

In a preferred embodiment, the temperature-registering elements are thermocouples mounted opposite to one another and located in the peripheral zone of the disc; the differential voltage of the thermocouples actuates a galvanometric relay, which supplies a constant current to an electric motor which can turn in both directions; the motor drives, if necessary, through a reduction gear, a screw with a fine pitch, the thread of which interacts with a moving nut, which nut acts on the disc through the agency of thrust ball-bearings.

It has been found that by using such a device to control the position of the disc inside the housing, it was possible, whatever the rate of supply demand of a given appliance, to keep at about two degrees the temperature differential existing between one side and the other of the disc, for the product to be treated, in the peripheral zone of the disc.

Figure 16:
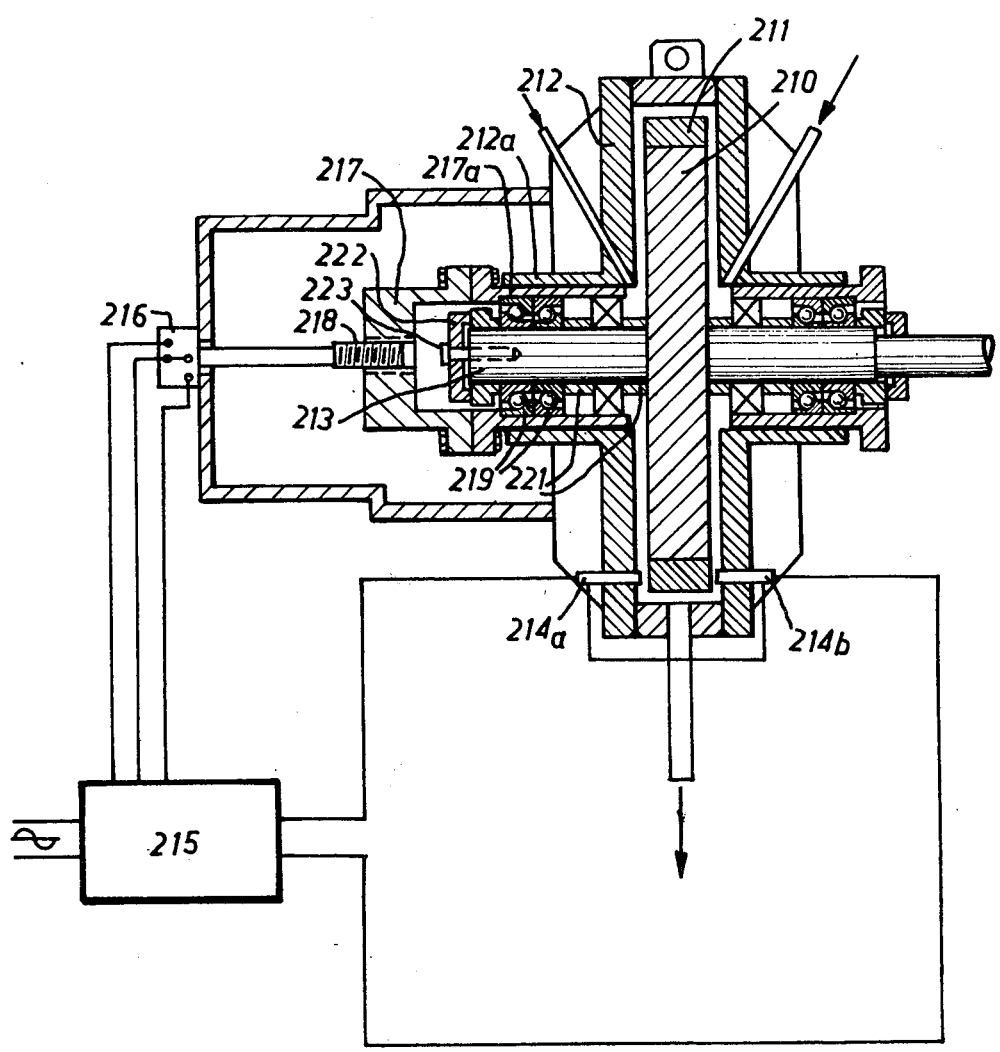
FIG. 16 is a sectional view of another embodiment of the invention.

FIG. 16 illustrates an embodiment of the invention which can be used for high throughputs of sterilized milk. Disc 210 is provided with peripheral binding ring 211. The external diameter of the disc 210 equipped with ring 211 is 300 mm. The disc 210 moves inside a housing 212, the gap between the housing and the faces of the disc being about 0.25 mm. The disc 210 is driven in a rotary movement by shaft 213 fitted inside a cylindrical sleeve formed by the cylindrical part 212a of the housing 212.

There are fitted to the two faces of the housing, at a distance of 5 mm from the periphery of the hoop ring 211 two iron-constantan thermo-couples 214a, 214b. The voltage obtained from the thermo-couples 214a, 214b are sent differentially to a galvanometric relay 215. The two thermo-couples 214a and 214b make it possible to obtain a difference in potential of 125 microvolts for a temperature differential of 2.5°. When a voltage differential above or equal to 100 microvolts is applied to the input of the relay 215, the latter puts out a current of 1 ampere at 220 volts to the terminals of an electric motor 216 which is able to rotate in either direction. The drive of the motor 216 is in one direction when the thermo-couple 214a has a voltage greater than that of the thermo-couple 214b, and in the opposite direction when the thermo-couple 214b, and in the opposite direction when the thermo-couple 214b produces a voltage greater than that of the thermo-couple 214a.

The motor 216 actuates a screw 218 with a fine pitch which interacts with the thread of nut 217 incorporating a cylindrical part 217a forming a sleeve which can slide freely inside the cylindrical part 212a of the housing 212. Two ball-bearings 219 are interposed between the sleeve 217a and the shaft 213. The position of the ball-bearings 219 in relation to the disc 210 is fixed by means of a spacer 221 and of a cap 222, which is made unitary with the shaft 213 by means of a screw 223.

It can be seen that this device makes it possible to control the position of the disc 210 in the interior of the housing 212 in dependence on the temperature differential existing between the two faces of the disc. It has been observed that with a device of this kind it is possible to obtain a temperature control of approximately 2° C even with high throughputs of sterilized milk. Thus, if for example, a set sterilizing temperature of 160° C is required, there is the certainty that the milk will not be subjected to a temperature higher than 160° at any point in the machine. On the other hand if the same appliance is used without control of the position of the disc, it has been observed that, for a speed of rotation of the disc of 5,200 r.p.m. with an input temperature of 25° C and an average discharge temperature of 160°, and for a treated throughput of about 300 l/min, the milk is brought on one face of the disc up to 140° C and on the other face up to 190° C. In that portion of the milk which has been subjected to the temperature of 190° C there is a destruction of certain proteins which imparts to the emergent milk a certain "cooked" taste. The control according to the invention entirely does away with that disadvantage.

It should be made clear that the temperature differential between the two faces of the disc is not observed with the device, such as illustrated in FIG. 16, even in the absence of control of the position of the disc when, for an input temperature of 25° C and a discharge temperature of 160° C, the speed of rotation is less than 3,600 r.p.m. and the throughput of milk treated is less than 100 liters an hour.

It will be appreciated from a reading of the foregoing specification that the invention provides a simple and practical apparatus that achieves complete sterilization of thermolabile substances without chemical modification of the substance, alteration of color or organoleptic qualities, and undesired physical changes.

Although the present invention has been described with specific reference to particular embodiments, the invention is not limited thereto, as there could be various modifications made without departing from the spirit or scope of this invention.

We claim:

1. An apparatus for sterilizing a product which may contain microorganisms, comprising:
    a first member and a second member, said two members having respective cooperating opposed substantially planar surfaces, said first member comprising a rotatable disc having an annular ring in gripping engagement with the disc around its periphery, said second member comprising a fixed housing within which said first member is disposed, said first member having two principal surfaces each of which is spaced from a corresponding substantially planar opposed surface of said housing;
    inlet means for the charging of said product into said space between said two opposed surfaces of said two members, said inlet means in said housing being in the area of the center of said first member;
    outlet means for said product flowing in the space between the surfaces of said first and second means; and
    driving means for driving at least one of said members about its axis to produce a linear peripheral speed of at least 50 meters per second and applying sufficient centrifugal force to said product to maintain it in liquid form under pressure and causing said product in said space to flow from the inlet to the outlet.

2. The apparatus of claim 1 wherein the annular ring has the same thickness as the disc.

3. The apparatus of claim 2 wherein the disc is made of a steel alloy characterized after heat treatment by a limit of elasticity of at least about 150 kg/mm$^2$.

4. The apparatus of claim 3 wherein the annular ring is made of the same steel alloy as the disc.

5. The apparatus of claim 1 wherein the edges between the lateral planar surfaces of the ring and the exterior peripheral face of the ring are rounded.

6. The apparatus of claim 1 in which the periphery of said housing adjacent to the periphery of said disc is immovably fixed and said housing is freely movable axially in the direction of the axis of said disc.

7. The apparatus of claim 6 wherein each side of said housing bears a cylindrical axial extension; an axial sleeve is slidably seated in each of said extensions; and the driving means for the disc comprises a shaft seated within each of said sleeves; said sleeves being capable of sliding freely relative to said housing.

8. The apparatus of claim 1 which includes two heat-sensitive means mounted opposite to each other on the planar opposed surfaces of the housing, relay means sensitive to and connected to said heat-sensitive means, and motor means for moving the disc axially, said motor means being controlled by said relay means.

9. The apparatus of claim 8 wherein the heat-sensitive elements are thermocouples mounted opposite each other in the peripheral zone of the housing.

10. The apparatus of claim 9 wherein the relay is galvanometric and actuatable by differential voltage produced by said thermocouples and the motor means is an electric motor capable of rotating in both directions and responsive to electric current produced by said relay.

* * * * *